US011514570B2

(12) United States Patent
Arita et al.

(10) Patent No.: US 11,514,570 B2
(45) Date of Patent: Nov. 29, 2022

(54) TEAR FLUID STATE EVALUATION METHOD, COMPUTER PROGRAM, AND DEVICE

(71) Applicant: KOWA COMPANY, LTD., Aichi (JP)

(72) Inventors: Reiko Arita, Saitama (JP); Katsumi Yabusaki, Tokyo (JP)

(73) Assignee: KOWA COMPANY, LTD., Aichi (JP)

( * ) Notice: Subject to any disclaimer, the term of this patent is extended or adjusted under 35 U.S.C. 154(b) by 32 days.

(21) Appl. No.: 16/637,216

(22) PCT Filed: Aug. 6, 2018

(86) PCT No.: PCT/JP2018/029324
§ 371 (c)(1),
(2) Date: Feb. 6, 2020

(87) PCT Pub. No.: WO2019/031424
PCT Pub. Date: Feb. 14, 2019

(65) Prior Publication Data
US 2020/0167915 A1    May 28, 2020

(30) Foreign Application Priority Data

Aug. 7, 2017 (JP) .............................. JP2017-152409

(51) Int. Cl.
*G06K 9/00* (2022.01)
*G06T 7/00* (2017.01)
(Continued)

(52) U.S. Cl.
CPC .......... *G06T 7/0012* (2013.01); *A61B 3/0025* (2013.01); *A61B 5/004* (2013.01);
(Continued)

(58) Field of Classification Search
None
See application file for complete search history.

(56) References Cited

U.S. PATENT DOCUMENTS 7,278,740 B1   10/2007   Suzuki et al.
7,413,304 B2    8/2008   Suzuki et al.
(Continued)

FOREIGN PATENT DOCUMENTS

CN    101208038 A    6/2008
CN    101667296 A    3/2010
(Continued)

OTHER PUBLICATIONS

Shen, Upper and Lower Tear Menisci in the Diagnosis of Dry Eye, Investigative Ophthalmology & Visual Science Jun. 2009, vol. 50, pp. 2722-2726. (Year: 2009).*

(Continued)

*Primary Examiner* — Wei Wen Yang
(74) *Attorney, Agent, or Firm* — McDermott Will & Emery LLP

(57) ABSTRACT

Provided are a method, a computer program and a device for noninvasively evaluating a state of a tear fluid and a tear fluid amount of a tear meniscus.
Included are a binarization step of binarizing a tear meniscus image, obtained by capturing at least a part of a tear meniscus of a subject, using a predetermined threshold value; an extraction step of extracting a high luminance region indicating a tear meniscus part from the binarized image; and an evaluation step of evaluating a tear fluid state on the basis of the high luminance region.

7 Claims, 5 Drawing Sheets

(51) Int. Cl.
*A61B 3/00* (2006.01)
*A61B 5/00* (2006.01)

(52) U.S. Cl.
CPC .. *A61B 5/0059* (2013.01); *G06T 2207/10024* (2013.01); *G06T 2207/30041* (2013.01)

(56) References Cited

U.S. PATENT DOCUMENTS

| | | |
|---|---|---|
| 7,654,669 B2 | 2/2010 | Suzuki |
| 8,649,583 B2 | 2/2014 | Tsukizawa et al. |
| 9,028,065 B2 | 5/2015 | Yokoi et al. |
| 2007/0171365 A1 | 7/2007 | Tuan |
| 2007/0237715 A1 | 10/2007 | Luce |
| 2007/0258043 A1 | 11/2007 | Suzuki et al. |
| 2008/0255474 A1 | 10/2008 | Ishida et al. |
| 2009/0225276 A1 | 9/2009 | Suzuki |
| 2010/0061637 A1 | 3/2010 | Mochizuki et al. |
| 2012/0177266 A1 | 7/2012 | Tsukizawa et al. |
| 2012/0300174 A1 | 11/2012 | Yokoi et al. |
| 2016/0249799 A1 | 9/2016 | Grenon et al. |
| 2017/0265740 A1* | 9/2017 | Grenon ............... A61B 3/1005 |

FOREIGN PATENT DOCUMENTS

| | | |
|---|---|---|
| CN | 102510734 A | 6/2012 |
| CN | 106510615 A | 3/2017 |
| CN | 106725282 A | 5/2017 |
| EP | 0943288 A1 | 9/1999 |
| EP | 1723900 A1 | 11/2006 |
| JP | 3896211 B2 | 3/2007 |
| JP | 2011-156030 A | 8/2011 |
| JP | 5138967 B2 | 2/2013 |
| JP | 2013-212363 A | 10/2013 |

OTHER PUBLICATIONS

Bartuzel (Automatic dynamic tear meniscus measurement in optical coherence tomography, Biomedical Optics Express, published Jul. 23, 2014, (C) 2014 OSA, pp. 2759-2768. (Year: 2014).*
"Dry Eye Diagnosis PPP (Prefered Pattern of Practice)," First edition, first printing, Medical View Co., Ltd. (publishing office), pp. 41-45, May 1, 2002, w/English translation.
International Search Report issued in International Patent Application No. PCT/JP2018/029324, dated Oct. 23, 2018, with English translation.
Extended European Search Report (EESR) dated Mar. 29, 2021 in European Application No. 18843382.5.
The First Office Action and Search Report received in corresponding CN Application No. 201880051230.7, dated Sep. 3, 2021.
Machine English Translation of The First Office Action and Search Report received in corresponding CN Application No. 201880051230.7, dated Sep. 3, 2021 (previously cited Nov. 11, 2021).
Second Office Action issued in corresponding Chinese Application No. 201880051230.7, dated Jan. 6, 2022 w/English Translation.

* cited by examiner

[FIG. 1]
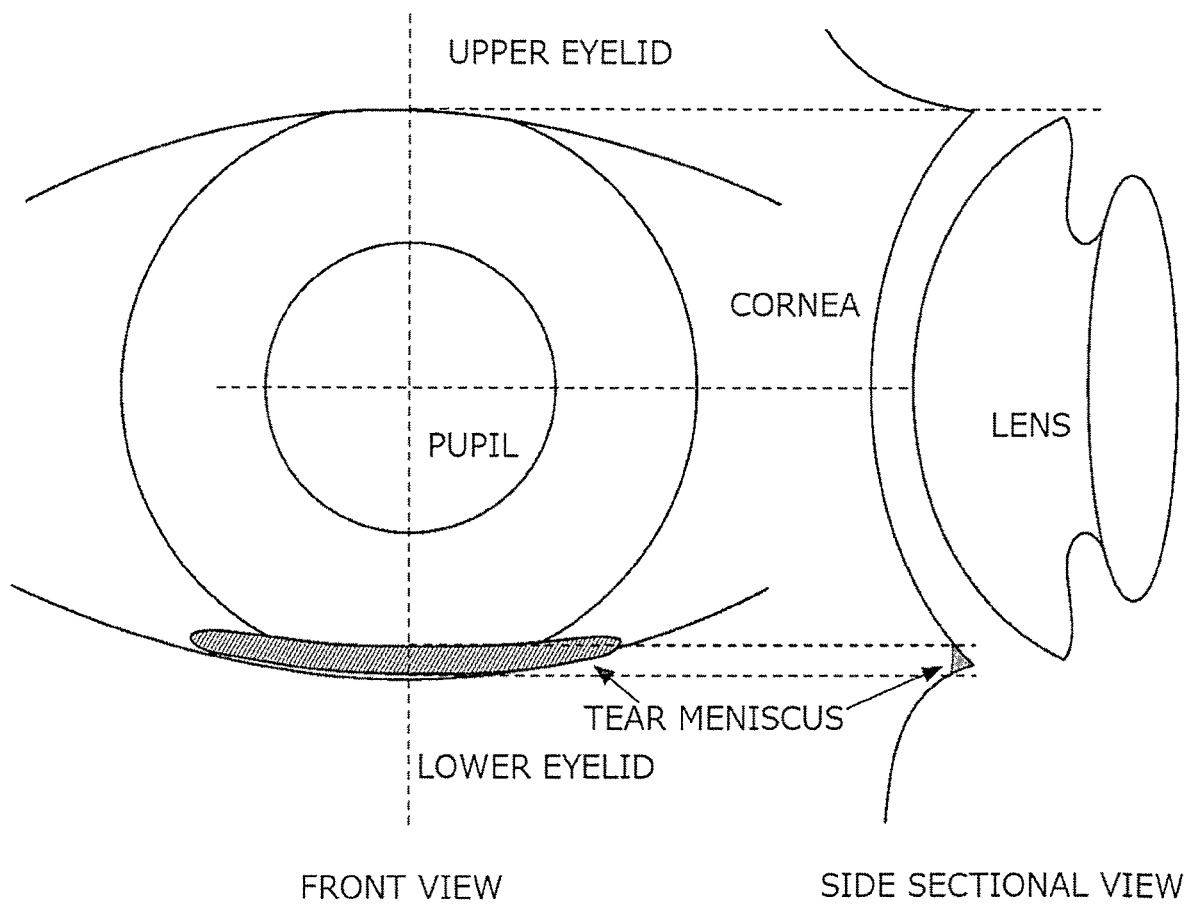

[FIG. 2]
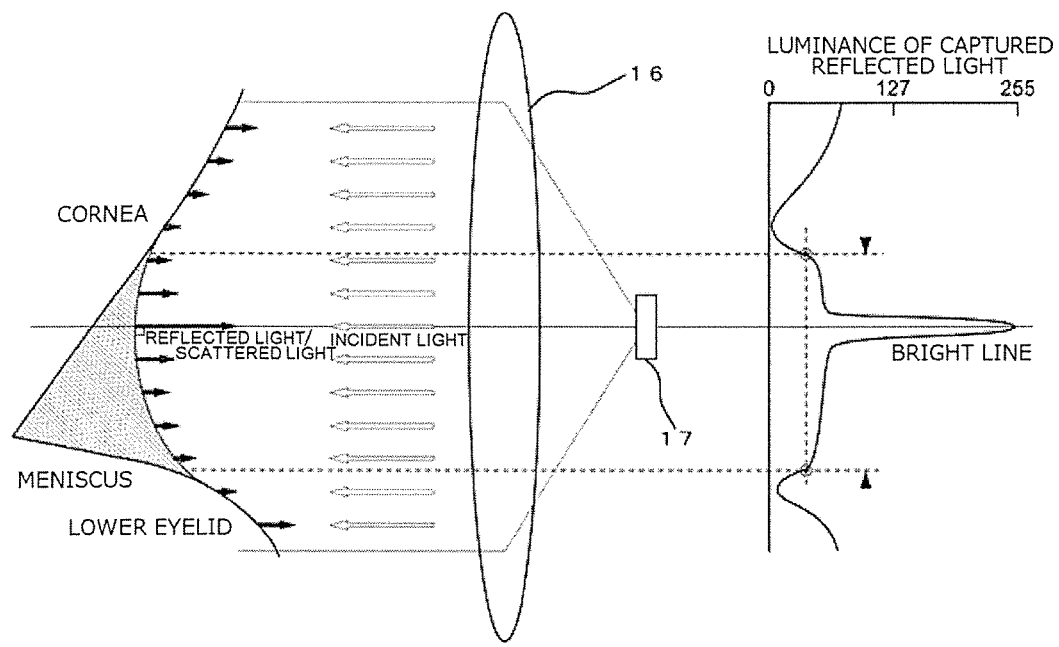

[FIG. 3]
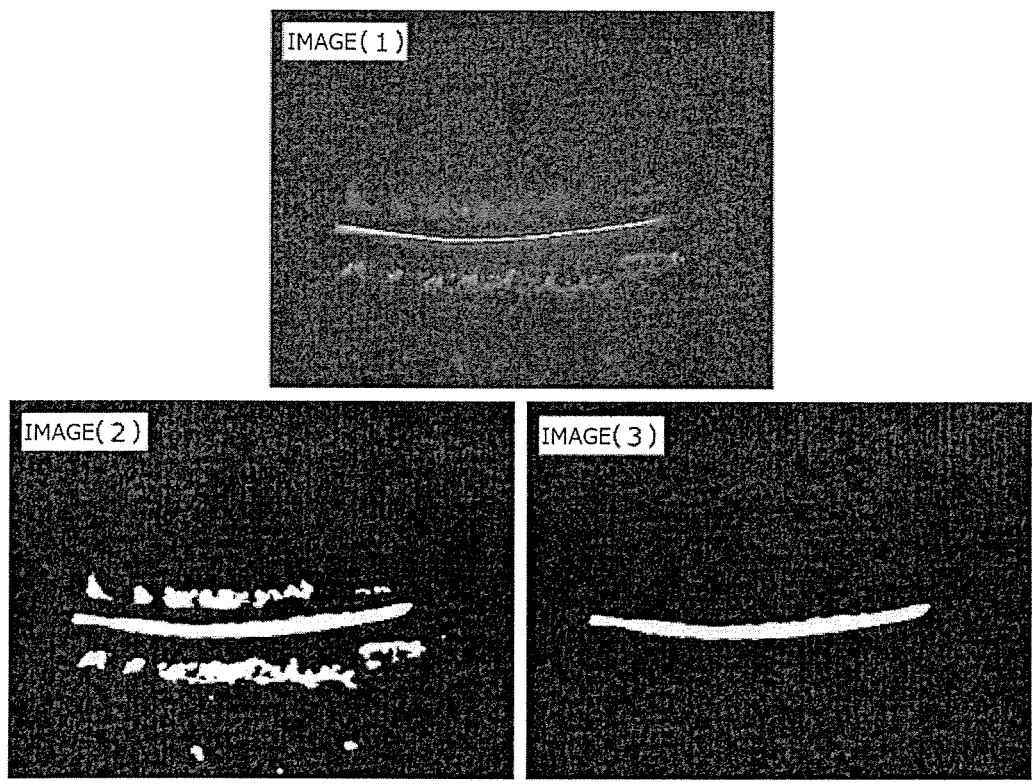

[FIG. 4]
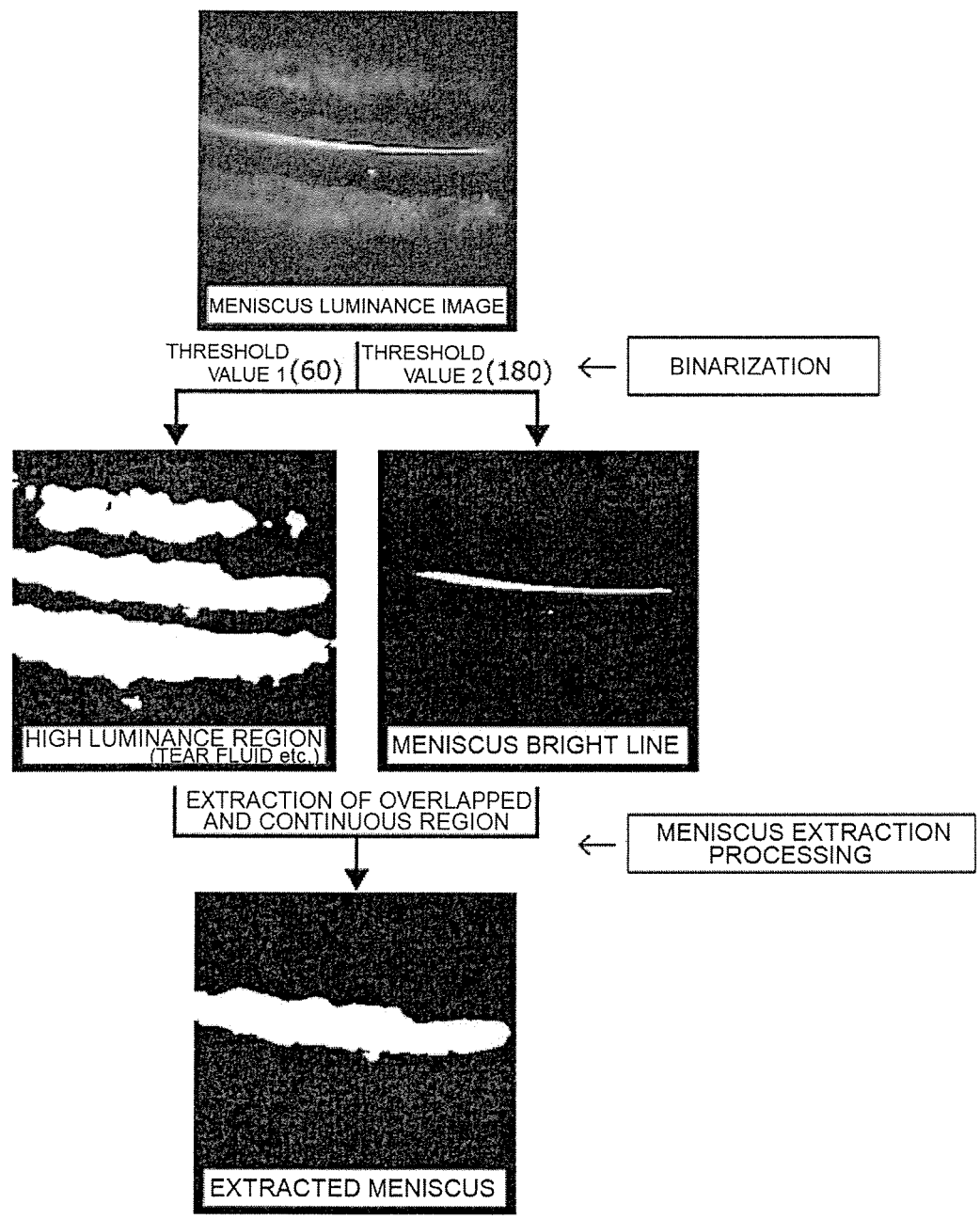

[FIG. 5]
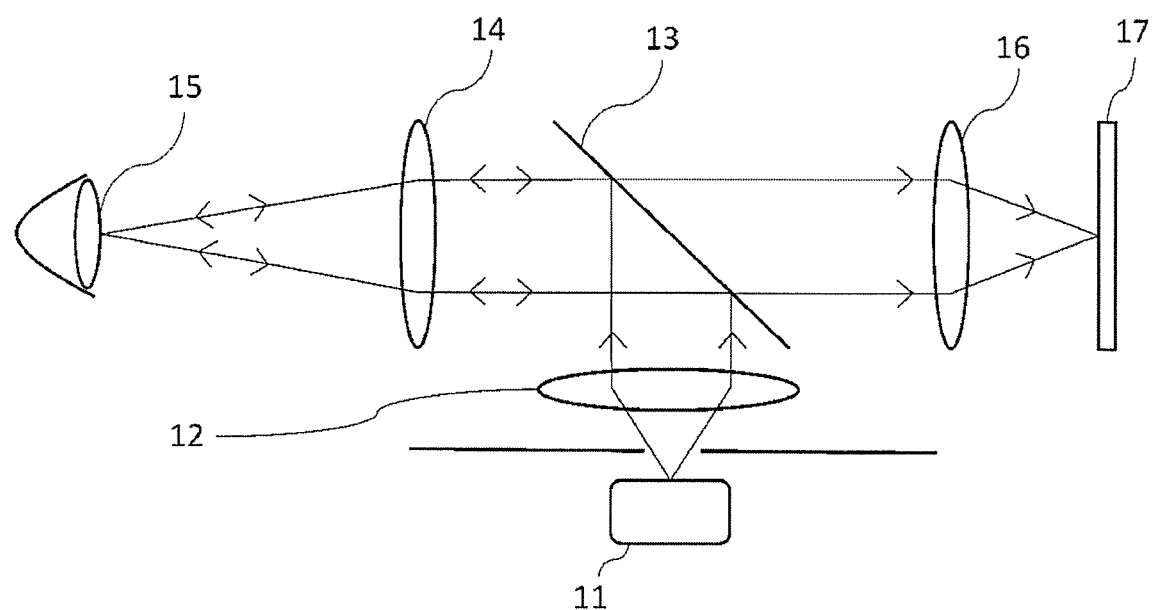

TEAR FLUID STATE EVALUATION METHOD, COMPUTER PROGRAM, AND DEVICE

CROSS-REFERENCE OF RELATED APPLICATIONS

This application is the U.S. National Phase under 35 U.S.C. § 371 of International Patent Application No. PCT/JP2018/029324, filed on Aug. 6, 2018, which in turn claims the benefit of Japanese Application No. 2017-152409, filed on Aug. 7, 2017, the entire disclosures of which Applications are incorporated by reference herein.

TECHNICAL FIELD

The present invention relates to a method, a computer program, and a device for evaluating a state of a tear fluid and a tear fluid amount, in particular, by analyzing an image of the tear meniscus.

BACKGROUND

An eyeball and an eyelid are protected by a tear fluid from entry of a foreign matter, drying, a damage due to friction, and the like. The tear fluid layer is composed of two layers, a liquid layer including water that occupies most of the tear fluid layer and a glycoprotein (mucin), and an oil layer covering the liquid layer. The oil layer prevents evaporation of the liquid layer by preventing the liquid layer from being in direct contact with the air. A component of the oil layer is secreted from the meibomian gland present in the eyelid. If the meibomian gland is damaged due to aging, inflammation, scratching, and the like, the oil layer is not properly formed, causing a symptom, so-called dry eye, due to failure to maintain the liquid layer.

As a method for determining dry eye, "Schirmer's test" and "BUT (Breakup time) test" are conventionally known. This "Schirmer's test" is a method in which a filter paper with a scale is placed between the conjunctiva and the lower eyelid, and, after maintaining this state for 5 minutes, an amount of the tear fluid absorbed in the filter paper after 5 minutes is quantitatively determined.

On the other hand, as described in Non-Patent Literature 1, in the "BUT test," a fluorescent dye melted in a liquid layer of the tear fluid layer such as fluorescein is applied to an eye, and, after the fluorescence is excited by excitation light, a time from opening the eyelid to the breakdown of the liquid layer of the tear fluid is measured by a stopwatch or the like.

Further, the tear fluid amount present in the tear meniscus is recognized as an important indicator for diagnosing dry eye. The tear meniscus, also called the tear meniscus, is formed by the tear fluid stored in a groove-shaped part from the side view located between the lower eyelid and the cornea as shown in FIG. 1. The tear fluid amount of the tear meniscus is measured and used as an indicator for the pathological diagnosis of dry eye and the like.

As to measurement of the tear fluid amount of the tear meniscus, there have been conventionally proposed various means. For example, as described in Patent Literature 1, a known examination tool includes a long, narrow body portion made from a synthetic resin or synthetic rubber in which a slit is formed and a water absorbing member disposed inside the slit. A tip portion of the examination tool is brought into contact with the lower eyelid of a subject to measure the tear fluid amount of the tear meniscus permeating into the water absorbing member.

Further, Patent Literature 2 proposes an ophthalmic measurement apparatus which quantitatively measures a physical quantity of the tear fluid amount of the tear meniscus and is used for the diagnosis of the dry eye condition. Specifically, the ophthalmic measurement apparatus includes a lattice forming a plurality of slit-like openings, a unit configured to project the openings onto the surface of the tear fluid accumulated in the lower eyelid, a unit configured to capture an image of the profected openings, and a unit configured to perform an arithmetic operation of the physical quantity of the tear fluid on the basis of the captured image of the openings. In the ophthalmic measurement apparatus, the directions of the lattice image in the center part and the lattice image in the peripheral part projected on the tear fluid surface are changed so as to make straight lines orthogonal to the lattice openings meet at a single point.

CITATION LIST

Patent Literature

Patent Literature 1: Japanese Patent No. 5138967
Patent Literature 2: Japanese Patent No. 3896211

Non-Patent Literature

Non-Patent Literature 1: "Dry Eye Diagnosis PPP (pp. 41 to 45)" (first edition, first printing: May 1, 2002, Edited by: Dry Eye Society, Publisher: Shunji Nakao, Publishing Office: Medical View Co., Ltd.)

SUMMARY OF INVENTION

Technical Problem

However, the "Schirmer's test" and the "BUT test" described above are basically an invasive method, which requires intrusion of the filter paper or the like or eye drop instillation of the fluorescent dye, thus likely causing a pain or discomfort to the subject. Similarly, the examination tool according to Patent Literature 1 is used in a method in which the tip is brought into contact with the tear meniscus of the subject, and this means that the tool and the method are invasive.

Further, the means shown in Patent Literature 2 requires a member such as the lattice for projecting the lattice image on the tear meniscus, resulting in an increase in cost. Further, an angle of the tear meniscus present between the lower eyelid and the cornea changes in a bow shape towards the tail of the eye, requiring additional labor of, for example, changing an angle of the lattice in accordance with the angle change of the tear meniscus in projecting the lattice image on the tear meniscus.

The present invention has been made in view of the conventional problems described above and an object of the present invention is to noninvasively evaluate a state of a tear fluid and a tear fluid amount of the tear meniscus without causing a pain or discomfort to the subject.

Solution to Problem

A tear fluid state evaluation method, computer program, and device according to the present invention include the following steps and means.

(1) The method, computer program, and device include a binarization step of binarizing a tear meniscus image, obtained by capturing at least a part of a tear meniscus of a subject, using a predetermined threshold value, an extraction step of extracting a high luminance region indicating a tear meniscus part from the binarized image, and an evaluation step of evaluating a tear fluid state on the basis of the high luminance region.

(2) In the (1) described above, the method, computer program, and device are characterized by including, when the tear meniscus image is a color image, a step of creating a luminance image of the tear meniscus image, and in that the binarization step is a step of binarizing the luminance image using a predetermined threshold value.

(3) In the (1) or (2) described above, the method, computer program, and device are characterized in that the binarization step is a step of binarizing the image on the basis of two different threshold values, and the extraction step is a step of extracting, from the high luminance regions in a first binary image on the basis of a lower one of the threshold values and in a second binary image on the basis of a higher one of the threshold values, a continuous high luminance region corresponding to the high luminance region of the first binary image.

(4) In the (1) or (2) described above, the method, computer program, and device are characterized in that the binarization step is a step of binarizing the image on the basis of a predetermined threshold value and a profile shape, and the extraction step is a step of extracting, as a high luminance region, a range that includes a peak portion of the profile and has luminance equal to or larger than the predetermined threshold value.

(5) In any of the (1) to (4) described above, the method, computer program, and device are characterized in that the evaluation step is a step of evaluating a level of the tear fluid amount of the tear meniscus on the basis of a width of the extracted high luminance region.

Advantageous Effects of Invention

The present invention is configured to evaluate the tear fluid of the tear meniscus by analyzing a captured cornea image without requiring intrusion of the filter paper or intrusion of the fluorescent dye and the examination tool to the eye of a subject. Thus, the tear fluid of the tear meniscus can be noninvasively evaluated without causing a pain or discomfort to the subject. Further, the device in use is made by a simple configuration without requiring a special component or the like or having a complicated configuration.

BRIEF DESCRIPTION OF DRAWINGS

FIG. 1 is a schematic diagram illustrating a front and a side of the human eye for explaining a tear meniscus.

FIG. 2 is a diagram illustrating a state in which the tear meniscus is imaged, as well as a tendency of received light luminance depending on positions.

FIG. 3 is a diagram in which an image 1 shows an example of a luminance image, an image 2 shows an example of an image after binarization, and an image 3 shows an example of an image obtained by extracting a high luminance region indicating a tear fluid storage portion of the tear meniscus.

FIG. 4 is a diagram illustrating an example of processing and a flow thereof in Second Embodiment according to the present invention.

FIG. 5 is a schematic diagram illustrating a configuration of an image acquiring device.

DESCRIPTION OF EMBODIMENTS

First Embodiment

<Acquisition of Tear Meniscus Image>

As a device for capturing the tear meniscus of a subject to acquire the image, a conventionally known device maybe appropriately used as long as it can record the captured image as digital data. For example, in the image acquisition device schematically shown in FIG. 5, a light beam, which has been emitted from a light source 11 and transmitted through a diaphragm, sequentially passes through a lens 12, a splitter 13, and an objective lens 14 and is condensed on a tear meniscus 15 of an anterior eye portion of a subject eye of a subject. Reflected light from the tear meniscus 15 of the anterior eye portion passes through the objective lens 14 and the splitter 13, so that an image is formed on an imaging element 17 via an imaging lens 16. Captured data of the image formed on the imaging element 17 are subjected to a predetermined processing by an image processing engine and converted to image data and moving image data.

The image acquisition device is physically or logically connected to a tear fluid evaluation device according to the present invention. The tear fluid evaluation device includes a processing unit configured to compute and process data and a storing unit configured to store the image data, moving image data, and other data acquired by the image acquisition device. The storing unit stores a computer program and predetermined data for implementing the present invention, while the processing unit processes data according to a predetermined instruction by the computer program and the like.

FIG. 2 is a diagram illustrating a state in which a tear meniscus image is acquired by the image acquiring device and a tendency of received light luminance in relation to a positionof the tearmeniscus. When the tear meniscus image is captured by focusing on the tear meniscus, light is regularly reflected by a surface of the tear fluid of the tear meniscus. As a result, the high luminance is acquired from the tear fluid storage portion also in the tear meniscus image.

On the other hand, the cornea portion and the lower eyelid, located near the tear meniscus in the upper and lower sides, respectively, have a shape rising from the tear meniscus toward the image acquiring device, causing a reduction in a reflected light intensity of light at these portions. Thus, the corresponding sites in the tear meniscus image are acquired as a dark part having a low luminance. In other parts of the cornea and the lower eyelid, the luminance is obtained in accordance with the reflected light intensity due to the curvature of the parts.

Processing of the tear meniscus image thus obtained will be described below.

<Luminance Image>

In a case where the tear meniscus image is acquired as a color image, processing of converting the color image to a grayscale image is performed to acquire a luminance image of the tear meniscus image. As a method for determining the luminance in each pixel of the grayscale image after conversion, a conventionally known method may be appropriately used. For example, the following methods are used.

First, "(a) a method of using the luminance of any of three color elements of R, G, and B (red, green, blue) in each pixel of the tear meniscus image as luminance in a corresponding pixel of the grayscale image" can be mentioned. Further, for example, "(b) a method of using a maximum value of the luminance of the color elements of R, G, and B," "(c) a method of using a minimum value of the luminance of the color elements of R, G, and B," "(d) a method of using an average of the luminance of at least two or more color elements," "(e) a method of using a median of the luminance of three color elements," and "(f) a method of using a value calculated by applying any of addition, subtraction, multiplication, and division to the luminance of two or more color elements" can be mentioned.

These methods can be appropriately used for determining the luminance in each pixel of the grayscale image. However, among the methods described above, "(b) the method of using a maximum value of the luminance of the color elements of R, G, and B" is particularly preferable.

The method of using a maximum value of the luminance of the color elements of R, G, and B is preferable because of the following reason. An image obtained by capturing the tear fluid on the cornea usually has large variations in color intensities depending on parts of the image due to appearance of interference fringe on the tear fluid. Thus, for example, in a method of using the luminance of red (R), among three color elements of R, G, and B (red, green, blue), as the luminance in a corresponding pixel of a grayscale image, there are disadvantages, such as the fact that an originally bright part having high intensities of other colors, green (G) and blue (B), is incorrectly converted as a dark part in the grayscale image due to the low luminance of red (R). Such a problem can be prevented in the above method.

An example of the luminance image obtained in this manner is shown as an "image (1)" in FIG. 3.

Note that the processing for creating the luminance image described above is performed when the tear meniscus image is captured and recorded as a color image by the image acquiring device. Thus, this processing is not necessary if the tear meniscus image acquired by the image acquiring device is an image in which the luminance in each pixel is originally determined by a single factor like a grayscale image.

<Binarization>

The luminance image described above is binarized by comparing a predetermined threshold value with a pixel of the luminance image to obtain a binary image. For example, each pixel of the luminance image obtained as described above only needs to be determined whether the pixel has the luminance equal to or larger than the predetermined threshold value (high luminance pixel) or the pixel has the luminance less than the threshold value (low luminance pixel).

The tear meniscus image is divided into two types of pixels, a high luminance pixel and a low luminance pixel, by this binarization. For making it visually apparent, the image may be distinguished by color, for example, the high luminance pixel is expressed in a white color and the low luminance pixel is expressed in a black color.

When classified by colors in this manner, the luminance image divided into the high luminance pixels and the low luminance pixels by binarization can be completely expressed by two colors. In this case, the pixels expressed in a white color means that a part showing the high luminance with a high reflected light intensity is extracted, that is, a part including the tear meniscus is extracted.

As the threshold value used for binarization, a predetermined fixed value may be used. However, each luminance image is different according to the state of illumination or the state of focusing, and thus, a dynamic value is preferably set so as to perform optimal binarization.

As a method for calculating the dynamic threshold value, for example, the threshold value may be an average value or a median of the luminance in all pixels of the luminance image, an intermediate value of the maximum and minimum luminance, or the like. However, without being limited to these methods, other known methods can also be appropriately used.

An example of the image after the binarization thus obtained is shown as an "image (2)" in FIG. 3.

<Extraction of Tear Meniscus Part>

Extraction of the tear meniscus part using the image after binarization will be described below. As a first method, the tear meniscus part usually appears as a linear pattern according to its shape. For example, in the image after binarization shown as the image (2) in FIG. 3, regions of the high luminance pixels (high luminance regions) expressed in a white color include a linear part corresponding to the tear meniscus part and regions scattered above and below the linear part. The high luminance regions present above and below the linear part are not the tear meniscus part and thus removed.

The image thus obtained is an extracted image of the tear meniscus part and an example of the extracted image is shown as an "image (3)" in FIG. 3.

Note that the binarization method and the extraction method of the tear meniscus part in the present invention are not limited to the methods described above, and various methods can be used. Examples thereof include a method in which, in a profile of the captured reflected light luminance, that is, a profile of the luminance in the image, shown in the right part of FIG. 2, binarization is performed to divide the profile into two regions, a relevant region and a non-relevant region, in accordance with the profile shape and a predetermined threshold value (indicated by "double circle" in the profile in the right part of FIG. 2), and the relevant region (between "inverted filled triangle" and "filled triangle" in the profile in the right part of FIG. 2) is extracted as the meniscus part in which the tear fluid is present. In this method, the predetermined threshold value may be set (as a dynamic threshold value) such that the relevant region is not connected to upper and lower parts outside a bright line and the height of the meniscus becomes maximum, as shown in the profile in the right part of FIG. 2. Alternatively, as the brightness differs depending on images, a threshold value that is fixed (fixed threshold value) may be used by normalizing the luminance in the image by the maximum value and the minimum value. Alternatively, a dynamic threshold value may be set from the luminance in the image without normalizing the luminance in the images. Further, fixed threshold values or dynamic threshold values different between upper and lower parts outside a bright line may be set. In these methods, a bright line part and slightly bright parts above and below the bright line part can be extracted as the meniscus part in which the tear fluid is present.

<Evaluation of Extracted Image of Tear Meniscus Part>

The extracted image of tear meniscus part obtained in the above manner shows a linear high luminance region indicating the tear meniscus part, and a level of the tear fluid amount can be determined by the width of the linear high luminance region. In general, an actual tear fluid amount can be determined to be high with the larger width of the high luminance region, while the tear fluid amount can be determined to be low with the smaller width of the high luminance region.

Specifically, the width of the high luminance region can be calculated from the number of pixels in the high luminance region in a vertical direction of the image. The width of the high luminance region differs depending on parts of the high luminance region. However, which part of the high luminance region is used to evaluate the width can be appropriately and freely determined.

Further, with accumulation of data showing a correlation between the width of the high luminance region indicating the tear meniscus part and the tear fluid amount of the tear meniscus, the tear fluid amount of the tear meniscus can be presumptively calculated from the width of the high luminance region by referring to the correlation data.

Further, if a break or a gap is found in the high luminance region appeared in a linear pattern, the state of the tear fluid (tear meniscus) in that vicinity can be determined to be undesirable.

Second Embodiment

The processing of binarization and extraction of the tear meniscus part has been described in First Embodiment. Another method thereof will be described below. In particular, a method for automatically extracting the tear meniscus part using the image after binarization will be described. Note that the processing that is not particularly referred to hereinbelow is the same as that in First Embodiment.

In the present embodiment, when binarization is performed on the luminance image obtained in the same manner as in First Embodiment, two different values are set as the threshold value and the binarization is performed using these threshold values to obtain the binary images.

As shown in FIG. 4, the binarization is performed on the luminance image using a threshold value 1 ("60" in an example shown in FIG. 4) to obtain a first binary image. Similarly, the binarization is performed on the luminance image using a threshold value 2 ("180" in an example shown in FIG. 4) to obtain a second binary image. The tear meniscus part is determined from an overlapped region of the high luminance regions in the first and second binary images thus obtained.

When two binary images are obtained from the luminance image using two threshold values having different values, the high luminance region shown in the binary image (the second binary image) using the higher one of the threshold values (the threshold value 2 in the above example) is always included in the high luminance region shown in the binary image (the first binary image) using the lower one of the threshold values (the threshold value 1 in the above example).

Thus, the tear meniscus part can be automatically detected by extracting the high luminance region in the first binary image that includes, and is continuous to, the high luminance region in the second binarization. For example, extraction of the high luminance region in the first binary image including the high luminance region in the second binary image may be performed as follows. Pixels in the second binary image corresponding to pixels showing a high luminance region in the first binary image are specified, and a high luminance region of the first binary image continuous to these specified pixels is extracted in relation to the second binary image.

Note that two threshold values having different values in the present Second Embodiment may be set as a predetermined fixed value or dynamically calculated and determined similarly to First Embodiment. As a method for dynamically determining the threshold value, in addition to the one mentioned above, the threshold value may be a value obtained by dividing a predetermined value from the maximum value of the luminance in the pixels of the luminance image or a value obtained by subtracting a predetermined ratio with respect to the maximum value from the maximum value (for example, a value calculated as 80% of the maximum value). On the other hand, the lower threshold value maybe a value obtained by adding a predetermined value to the minimum value of the luminance in the pixels of the luminance image or a value obtained by increasing a predetermined ratio from the minimum value (for example, a value calculated as 120% of the minimum value).

While the present invention has been described above, it is to be understood that the present invention is not limited to the embodiments described above and may be modified and embodied in various aspects.

As described above, the luminance (or brightness) in the pixel is preferably used for creating the luminance image. However, without being limited to this, saturation or the like maybe used. Further, calculation of the aforementioned various numerical values is not limited to the calculation methods described above, and an arithmetic operation using a known method can be appropriately performed to calculate a more suitable value.

INDUSTRIAL APPLICABILITY

The present invention makes it possible to noninvasively confirm the state of the tear meniscus, in particular, a level of the tear fluid amount of the tear meniscus, and further makes it possible to estimate the tear fluid amount of the tear meniscus, without actually invasively measuring the tear fluid amount, by accumulating the correlation data between the width of the finally extracted high luminance region corresponding to the tear fluid storage portion and the actual tear fluid amount. As a result, the present invention contributes to noninvasive diagnosis or the like of dry eye and other conditions.

The invention claimed is:

1. A tear fluid state evaluation method comprising:
   obtaining a tear meniscus image by illuminating at least a part of a tear meniscus of a subject and receiving reflected light from at least the part of the tear meniscus,
   a binarization step of binarizing the tear meniscus image using a predetermined threshold value;
   an extraction step of extracting a high luminance region indicating a tear meniscus part from the binarized image; and
   an evaluation step of evaluating a tear fluid state on a basis of the high luminance region,
   wherein, the binarization step is a step of binarizing the image on a basis of two different threshold values, and
   the extraction step is a step of extracting, from the high luminance regions in a first binary image on a basis of a lower one of the threshold values and in a second binary image on a basis of a higher one of the threshold values, a continuous high luminance region corresponding to the high luminance region of the first binary image.

2. The tear fluid state evaluation method according to claim 1, comprising, when the tear meniscus image is a color image, a step of creating a luminance image of the tear meniscus image, wherein
   the binarization step is a step of binarizing the luminance image using a predetermined threshold value.

3. The tear fluid state evaluation method according to claim 1, wherein the binarization step is a step of binarizing the image on a basis of a predetermined threshold value and a profile shape of luminance of a tear meniscus image, and the extraction step is a step of extracting, as a high luminance region, a range that includes a peak portion of the profile and has luminance equal to or larger than the predetermined threshold value.

4. The tear fluid state evaluation method according to claim 1, wherein the evaluation step is a step of evaluating a level of the tear fluid amount of the tear meniscus on a basis of a width of the extracted high luminance region.

5. A non-transitory computer readable storage medium storing a computer program for causing a computer to execute the respective steps according to claim 1.

6. A tear fluid state evaluation device executing the method according to claim 1.

7. The tear fluid state evaluation method according to claim 1, wherein a lower portion or an upper portion of an eye of the subject is illuminated to obtain the tear meniscus image.

* * * * *